(12) United States Patent
King-Underwood et al.

(10) Patent No.: US 10,028,959 B2
(45) Date of Patent: *Jul. 24, 2018

(54) QUINAZOLIN-4 (3H)-ONE DERIVATIVES USED AS P13 KINASE INHIBITORS

(71) Applicant: Respivert Limited, Buckinghamshire (GB)

(72) Inventors: John King-Underwood, Pendock (GB); Kazuhiro Ito, Wallington (GB); Peter John Murray, Cheltenham (GB); George Hardy, Robertsbridge (GB); Frederick Arthur Brookfield, Benson (GB); Christopher John Brown, Abingdon (GB)

(73) Assignee: Respivert Ltd., Buckinghamshire (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/474,059

(22) Filed: Mar. 30, 2017

(65) Prior Publication Data

US 2017/0202841 A1 Jul. 20, 2017

Related U.S. Application Data

(63) Continuation of application No. 15/092,707, filed on Apr. 7, 2016, now Pat. No. 9,637,494, which is a continuation of application No. 13/865,379, filed on Apr. 18, 2013, now Pat. No. 9,340,545, which is a continuation of application No. PCT/GB2011/052015, filed on Oct. 18, 2011.

(51) Int. Cl.
| | | |
|---|---|---|
| *A01N 43/90* | (2006.01) | |
| *A61K 31/519* | (2006.01) | |
| *A61K 9/14* | (2006.01) | |
| *A61K 9/00* | (2006.01) | |
| *A61K 47/26* | (2006.01) | |

(52) U.S. Cl.
CPC .......... *A61K 31/519* (2013.01); *A61K 9/0075* (2013.01); *A61K 9/14* (2013.01); *A61K 47/26* (2013.01)

(58) Field of Classification Search
None
See application file for complete search history.

(56) References Cited

U.S. PATENT DOCUMENTS

| | | |
|---|---|---|
| 7,186,401 B2 | 3/2007 | Manfred et al. |
| 8,741,909 B2 | 6/2014 | King-Underwood et al. |
| 9,340,545 B2 * | 5/2016 | King-Underwood ... C07D 487/04 |
| 2006/0239932 A1 | 10/2006 | Monteith et al. |
| 2007/0037805 A1 | 2/2007 | Hayakawa et al. |
| 2011/0135655 A1 | 6/2011 | Katsikis et al. |
| 2012/0082727 A1 | 4/2012 | Cocconi et al. |

FOREIGN PATENT DOCUMENTS

| | | |
|---|---|---|
| CA | 2347856 | 5/2000 |
| EP | 1232745 A1 | 8/2002 |
| EP | 1604981 | 12/2005 |
| EP | 1661879 | 5/2006 |
| EP | 1829533 A2 | 9/2007 |
| EP | 1277738 | 3/2011 |
| EP | 2311434 A1 | 4/2011 |
| EP | 1790637 | 1/2014 |
| WO | WO 87/05213 A1 | 9/1987 |
| WO | WO 00/28979 A1 | 5/2000 |
| WO | WO 00/42042 | 7/2000 |

(Continued)

OTHER PUBLICATIONS

Ramen, L. E. and Cantley, L. C. "The Role of Phosphoinositide 3-Kinase Lipid Products in Cell Function", *J. Biol. Chem.*, 1999, 274:8347-8350.
Ito, K. et al., "Therapeutic Potential of Phosphatidylinositol 3-Kinase Inhibitors in Inflammatory Respiratory Disease", *J Pharmacol. Exp. Ther.*, 2007, 321:1-8.
Lee, K. S. et al., "Phosphoinositide 3-kinase-δ inhibitor recudes vascular permeability in a murine model of asthma", *J. Allergy Clin. Immunol.*, 2006, 118:403-409.
Lee, K. S. et al.,"Inhibition of phosphoinositide δ attenuates allergic airway inflammation and hyperresponsiveness in murine asthma model", 3-kinase *FASEB J.*, 2006, 20:455-65.
Sadhu, .et al., "Selective role of PI3K δ in neutrophil inflammatory responses", *Biochem. Biophys. Res. Commun.*, 2003, 308:764-9.

(Continued)

*Primary Examiner* — Jeffrey H Murray
(74) *Attorney, Agent, or Firm* — Ada O. Wong

(57) ABSTRACT

The present invention relates to the compound of formula (I)

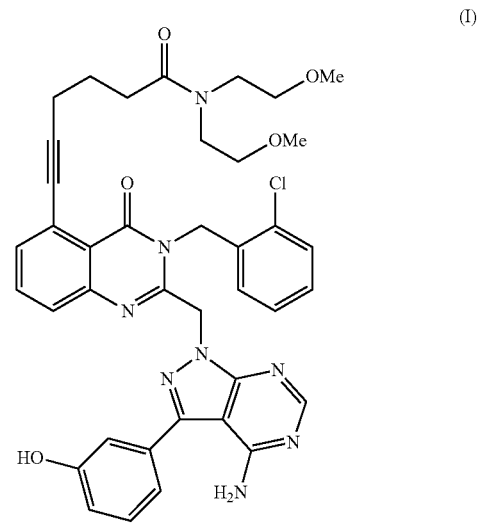

and to compositions comprising the same and to the use of the compound and to compositions of the compound in treatment, for example in the treatment of inflammatory diseases, in particular respiratory inflammatory disease. The invention also extends to methods of making the said compound.

5 Claims, No Drawings

(56) References Cited

FOREIGN PATENT DOCUMENTS

| | | |
|---|---|---|
| WO | WO 2000/053157 A1 | 9/2000 |
| WO | WO 01/81346 | 11/2001 |
| WO | WO 01/83456 | 11/2001 |
| WO | WO 2002/051831 | 7/2002 |
| WO | WO 03/007955 | 1/2003 |
| WO | WO 2003/006628 | 1/2003 |
| WO | WO 03/035075 | 5/2003 |
| WO | WO 2004/037176 | 5/2004 |
| WO | WO 2004/080966 | 9/2004 |
| WO | WO 2004/083174 | 9/2004 |
| WO | WO 2004/089988 A2 | 10/2004 |
| WO | WO 2005/007085 | 1/2005 |
| WO | WO 2005/012221 | 2/2005 |
| WO | WO 2005/016348 | 2/2005 |
| WO | WO 2005/016349 | 2/2005 |
| WO | WO 2005/046636 A1 | 5/2005 |
| WO | WO 2005/067901 | 7/2005 |
| WO | WO 2005/112935 | 12/2005 |
| WO | WO 2005/113554 | 12/2005 |
| WO | WO 2005/113556 | 12/2005 |
| WO | WO 2005/113556 A1 | 12/2005 |
| WO | WO 2005/117889 | 12/2005 |
| WO | WO 2005/120511 | 12/2005 |
| WO | WO 2006/030925 | 3/2006 |
| WO | WO 2006/089106 | 8/2006 |
| WO | WO 2007/068443 A1 | 6/2007 |
| WO | WO 2007/114926 A2 | 10/2007 |
| WO | WO 2007/134876 A2 | 11/2007 |
| WO | WO 2008/005262 | 1/2008 |
| WO | WO 2008/058402 | 5/2008 |
| WO | WO 2008/058691 A2 | 5/2008 |
| WO | WO 2008/067219 | 6/2008 |
| WO | WO 2008/104077 | 9/2008 |
| WO | WO 2008/127226 | 10/2008 |
| WO | WO 2008/138834 A1 | 11/2008 |
| WO | WO 2008/140750 | 11/2008 |
| WO | WO 2009/088986 | 7/2009 |
| WO | WO 2009/088990 | 7/2009 |
| WO | WO 2010008847 A2 | 1/2010 |
| WO | WO 2010008847 A3 | 1/2010 |
| WO | WO 2010/036380 A1 | 4/2010 |
| WO | WO 2010/059593 | 5/2010 |
| WO | WO 2010/065923 A2 | 6/2010 |
| WO | WO 2010/065932 A1 | 6/2010 |
| WO | WO 2010/111432 | 9/2010 |
| WO | WO 2011/015037 | 2/2011 |
| WO | WO 2011/048111 | 4/2011 |
| WO | WO 2011041399 A2 | 4/2011 |
| WO | WO 2012/052753 A1 | 4/2012 |
| WO | WO 2013/136075 A1 | 9/2013 |
| WO | WO 2013/136076 A1 | 9/2013 |

OTHER PUBLICATIONS

Doukas, J. et al., "Aerosolized Phosphoinositide 3-Kinase γ δ Inhibitor TG100-115 {3-{2,4-Diamino-6-(3-hydroxyphenyl)pteridin-7-yl}phenol} as a Therapeutic Candidate for Asthma and Chronic Obstructive Pulmonary Disease" , *J Pharmacol. Exp. Ther.*, 2009, 328:758-765.

To, Y. et al., "Targeting Phosphoinositide-3-Kinase-δ with Theophylline Reserves Corticosteriod Insensitivity in Chronic Obstructive Polmonary Disease", *Am. J. Respir. Crit. Care Med.*, 2010, 182:897-904.

Gautier et al., "Contribution à l'étude des ethers-0xydes propargyliques", Annales Pharmaceutigues Francaises, 1971, 29, 39-50.

Medicherla, S. et al., "p38α-Selective Mitogen-Activated Protein Kinase Inhibitor Sd-282 Reduces Inflammation in a Subchronic Model of Tobacco smole-Induced Airway Inflammation", J. Pharmacol. Exp. Ther 2008, 342:921-9.

Shah et al, "Evaluation of Two New Tablet Lubricants—Sodium Stearyl Furnarate and Glyceryl Behenate. Measurement of Physical Parameters (Compaction, Ejection and Residual Forces) in the Tableting Process and the Effect on the Dissolution Rate", Drug development and Industrial pharmacy 1986, vol. 12 No. 8-9, pp. 1329-1346.

Brittain, H.G., Polymorphism in Pharmaceutical Solids (Second Edition), 2009, vol. 192; ISBN:97814200731218/1420073214; pp. 1-5; 14-19; 88-95; 120-121; 234-237; 240-241; 318-346; 347-380 and 381-430.

Jordan, V. C., "Tamoxifen:A Most Unlikely Pioneering Medicine", Nature Reviews; Drug Discovery, 2; 2003, p. 2005.

Hackman, et al., "Translation of Research Evidence From Animals to Humans", JAMA, 296(14), 2006, p. 1731-1732.

Khimicheskaya Encyclopedia (Chemical Encyclopedia), vol. 4, pp. 990-993, Sovetskaya Entsiklopediya Moscov, 1988.

Knight et al., Cell, vol. 125, 2006, pp. 733-747.

Aspel et al., Nature Chemical Biology, vol. 4, 2008, pp. 691-699.

Laplante, et al., "Assessing Atropisomer Axial Chemistry Chirality in Drug Discovery and Development", Journal of Medicinal Chemistry, 2011; vol. 54, pp. 7005-7011.

Brana, et al., BMC Medicine, vol. 10: 161, p. 1-15, 2012.

Thomas, et al., Current Opinion in Pharmacology, vol. 8, pp. 267-274, 2008.

Clayden et al., "The Challenge of Atropisomerism in Drug Discovery", Agnew, Chem. Int. Ed. 2009; vol. 48, pp. 6398-6401.

Opposition lodged against corresponding Costa Rican Application No. dated Jul. 4, 2017.

\* cited by examiner

QUINAZOLIN-4 (3H)-ONE DERIVATIVES USED AS PI3 KINASE INHIBITORS

CROSS-REFERENCE TO RELATED APPLICATIONS

This application is a continuation of U.S. Ser. No. 15/092,707 filed Apr. 7, 2016, currently allowed, which is a continuation of U.S. Ser. No. 13/865,379, filed Apr. 18, 2013, now U.S. Pat. No. 9,340,545, which is a continuation of PCT International Patent Application No. PCT/GB2011/052015, filed Oct. 18, 2011, which claims priority to TW Patent Application No. 099135360 filed Oct. 18, 2010, and PCT International Patent Application No. PCT/EP2010/065746, Filed Oct. 19, 2010, the contents of each of which are hereby incorporated by reference in their entirety.

FIELD OF THE INVENTION

The invention relates to a compound that inhibits phosphoinositide 3-kinases, (PI3 kinases). In particular the invention relates to a compound that inhibits the PI3 kinase delta sub-type and, in addition, the gamma and alpha sub-types thereof, and to its use in therapy, including in pharmaceutical combinations, especially in the treatment of inflammatory diseases, including inflammatory diseases of the lung, such as COPD and asthma. The disclosure also extends to methods of preparing the said compound and pharmaceutical compositions comprising same.

BACKGROUND OF THE INVENTION

Lipid kinases catalyse the phosphorylation of lipids to produce species involved in the regulation of a wide range of physiological processes, including cellular migration and adhesion. The PI3-kinases are membrane associated proteins and belong to this class of enzymes which catalyse the phosphorylation of lipids which are themselves associated with cell membranes. The PI3-kinase delta (δ) isozyme (PI3 kinase δ) is one of four isoforms of type I PI3 kinases responsible for generating various 3'-phosphorylated phosphoinositides, that mediate cellular signalling and have been implicated in a number of cellular processes such as inflammation, growth factor signalling, malignant transformation and immunity [See Review by Rameh, L. E. and Cantley, L. C. *J. Biol. Chem.*, 1999, 274:8347-8350].

Involvement of PI3 kinases in controlling inflammation has been confirmed in several models using pan-PI3 kinase inhibitors, such as LY-294002 and wortmannin [Ito, K. et al., *J Pharmacol. Exp. Ther.*, 2007, 321:1-8]. Recent studies have been conducted using either selective PI3 kinase inhibitors or in knock-out mice lacking a specific enzyme isoform. These studies have demonstrated the role of pathways controlled by PI3 kinase enzymes in inflammation. The PI3 kinase δ selective inhibitor IC-87114 was found to inhibit airways hyper-responsiveness, IgE release, pro-inflammatory cytokine expression, inflammatory cell accumulation into the lung and vascular permeability in ovalbumin-sensitized, ovalbumin-challenged mice [Lee, K. S. et al., *J. Allergy Clin. Immunol.*, 2006, 118:403-409 and Lee, K. S. et al., *FASEB J.*, 2006, 20:455-65]. In addition, IC-87114 lowered neutrophil accumulation in the lungs of mice and neutrophil function, stimulated by TNFα [Sadhu, C. et al., *Biochem. Biophys. Res. Commun.*, 2003, 308:764-9]. The PI3 kinase δ isoform is activated by insulin and other growth factors, as well as by G-protein coupled protein signaling and inflammatory cytokines. Recently the PI3 kinase dual δ/γ inhibitor TG100-115 was reported to inhibit pulmonary eosinophilia and interleukin-13 as well as mucin accumulation and airways hyperresponsiveness in a murine model, when administered by aerosolisation. The same authors also reported that the compound was able to inhibit pulmonary neutrophilia elicited by either LPS or cigarette smoke [Doukas, J. et al., *J Pharmacol. Exp. Ther.*, 2009, 328:758-765]

Since it is also activated by oxidative stress, the PI3 kinase δ isoform is likely to be relevant as a target for therapeutic intervention in those diseases where a high level of oxidative stress is implicated. Downstream mediators of the PI3 kinase signal transduction pathway include Akt (a serine/threonine protein kinase) and the mammalian target of rapamycin, the enzyme mTOR. Recent work has suggested that activation of PI3 kinase δ, leading to phosphorylation of Akt, is able to induce a state of corticosteroid resistance in otherwise corticosteroid-sensitive cells [To, Y. et al., *Am. J. Respir. Crit. Care Med.*, 2010, 182:897-904]. These observations have led to the hypothesis that this signalling cascade could be one mechanism responsible for the corticosteroid-insensitivity of inflammation observed in the lungs of patients suffering from COPD, as well as those asthmatics who smoke, thereby subjecting their lungs to increased oxidative stress. Indeed, theophylline, a compound used in the treatment of both COPD and asthma, has been suggested to reverse steroid insensitivity through mechanisms involving interaction with pathways controlled by PI3 kinase δ [To, Y. et al., *Am. J. Respir. Crit. Care Med.*, 2010, 182:897-904].

At present the mainstay of treatment for both asthma and COPD is inhaled therapy, using a combination of corticosteroids, muscarinic antagonists and $\beta_2$-agonists, as judged clinically appropriate. One way of addressing the unmet medical needs in COPD and asthma is to identify new therapeutic agents, for example suitable for use as inhaled medicines, which have the potential to provide significant benefit when used as a monotherapy or in combination with one or more medicaments from these three pharmacological classes. Therefore, there remains a need to identify and develop isoform selective PI3 kinase inhibitors which have the potential to provide enhanced therapeutic efficacy in asthma, COPD and other inflammatory diseases.

SUMMARY OF THE INVENTION

According to the invention, there is provided a compound of formula (I):

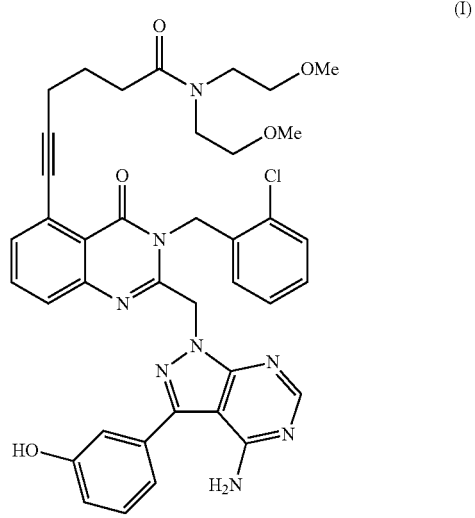 [SMILES: COCCN(CCOC)C(=O)CCCC#Cc1cccc2nc(Cn3nc(-c4cccc(O)c4)c4c(N)ncnc43)n(Cc3ccccc3Cl)c(=O)c12]

that is 6-(2-((4-amino-3-(3-hydroxyphenyl)-1H-pyrazolo[3,4-d]pyrimidin-1-yl)methyl)-3-(2-chlorobenzyl)-4-oxo-3,4-dihydroquinazolin-5-yl)-N,N-bis(2-methoxyethyl)hex-5-ynamide or a pharmaceutically acceptable salt thereof, including all stereoisomers, tautomers and isotopic derivatives thereof.

The compound of the present disclosure is a dual PI3K delta PI3K gamma inhibitor.

The term inhibitor as employed herein is intended to refer to a compound that reduces (for example by at least 50%) or eliminates the biological activity of the target protein, for example the PI3K delta isozyme, in an in vitro enzyme assay.

The term delta/gamma inhibitor as employed herein is intended to refer to the fact that the compound inhibits, to some degree, both enzyme isoforms although not necessarily to the same extent.

The compound of the present disclosure is active in cell based screening systems and thereby demonstrates that it possesses suitable properties for penetrating cells and thereby exert intracellular pharmacological effects.

The compound of the present disclosure has therapeutically relevant and desirable pharmaceutical properties, for example adequate stability, solubility and potent activity.

In one embodiment there is provided a pharmaceutically acceptable acid addition salt of the compound of the invention.

The pharmaceutically acceptable acid addition salts as mentioned hereinabove are meant to comprise the therapeutically active, non-toxic, acid addition salts that the compound of formula (I) is able to form. These pharmaceutically acceptable acid addition salts can conveniently be obtained by treating the free base form of the compound of formula (I) with such appropriate acid. Appropriate acids comprise, for example, inorganic acids such as hydrochloric acid, hydrobromic acid, and sulfuric, and phosphoric acids and the like; or organic acids such as, for example, acetic, propanoic, hydroxyacetic, lactic, malonic, succinic, maleic, fumaric, malic, tartaric, citric, methanesulfonic, para-toluenesulfonic, cyclamic, salicylic, para-aminosalicylic, pamoic acid and the like.

Examples of salts of compound (I) include all pharmaceutically acceptable salts, such as, without limitation, acid addition salts of mineral acids such as HCl and HBr salts and addition salts of organic acids such as a methanesulfonic acid salt. Further examples include sulphuric acid salts and phosphoric acid salts.

In one embodiment there is provided 6-(2-((4-amino-3-(3-hydroxyphenyl)-1H-pyrazolo[3,4-d]pyrimidin-1-yl)methyl)-3-(2-chlorobenzyl)-4-oxo-3,4-dihydroquinazolin-5-yl)-N,N-bis(2-methoxyethyl)hex-5-ynamide hydrochloride.

In one embodiment there is provided 6-(2-((4-amino-3-(3-hydroxyphenyl)-1H-pyrazolo[3,4-d]pyrimidin-1-yl)methyl)-3-(2-chlorobenzyl)-4-oxo-3,4-dihydroquinazolin-5-yl)-N,N-bis(2-methoxyethyl)hex-5-ynamide hydrobromide.

In one embodiment there is provided 6-(2-((4-amino-3-(3-hydroxyphenyl)-1H-pyrazolo[3,4-d]pyrimidin-1-yl)methyl)-3-(2-chlorobenzyl)-4-oxo-3,4-dihydroquinazolin-5-yl)-N,N-bis(2-methoxyethyl)hex-5-ynamide tosylate.

The disclosure also extends to solvates of the compounds herein. Examples of solvates include hydrates.

The compounds of the disclosure include those where the atom specified is a naturally occurring or non-naturally occurring isotope. In one embodiment the isotope is a stable isotope. Thus the compounds of the disclosure include, for example those containing one or more deuterium atoms in place of hydrogen atoms and the like.

In one embodiment of the invention wherein the compound of formula (I) is a deuterium labelled compound, the isotopically labelled compound is the hexadeuterio derivative of formula (IA).

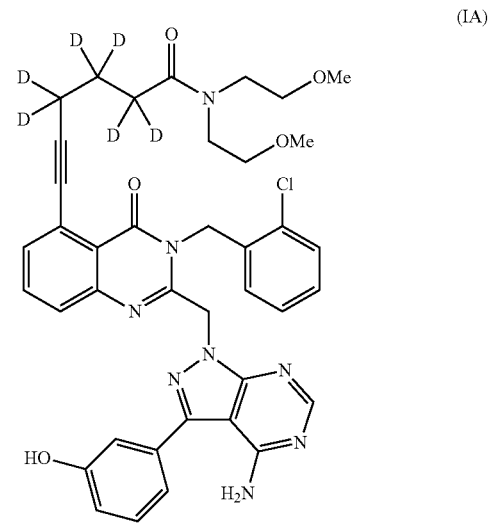 [SMILES: [2H]C([2H])(C#Cc1cccc2nc(Cn3nc(-c4cccc(O)c4)c4c(N)ncnc43)n(Cc3ccccc3Cl)c(=O)c12)C([2H])([2H])C([2H])([2H])C(=O)N(CCOC)CCOC]

(IA)

The disclosure also extends to all polymorphic forms of the compounds herein defined.

The compound of formula (I) may be conveniently prepared by a process comprising reacting a compound of formula (II):

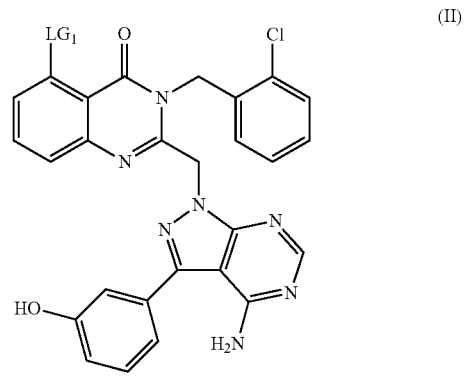

(II)

or a protected derivate thereof wherein LG$_1$ represents a leaving group such as halo, in particular bromo, with a compound of formula (III):

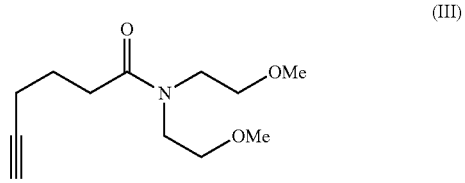 [SMILES: C#CCCCC(=O)N(CCOC)CCOC]

(III)

in the presence of a suitable catalyst and an organic base and in a polar aprotic solvent under an inert atmosphere. Suitable catalysts include palladium catalysts such as bis(triphenyl-phosphine)palladium (II) dichloride, in the presence of copper iodide and a suitable polar aprotic solvent is DMF. A suitable inert atmosphere is nitrogen.

Alternatively the compound of formula (I) may be prepared by a process comprising of reacting a compound of formula (II) or a protected derivative thereof with a compound of formula (IV):

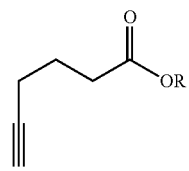

(IV)

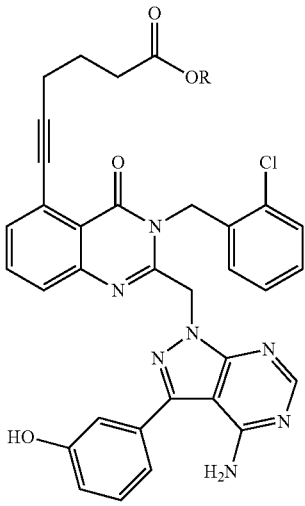

(V)

wherein R is suitably H to provide a compound of formula (V) or a protected derivative thereof. The compound of formula (I) is then obtained from the compound of formula (V) by one or more standard functional group transformations. For example where R is H the compound of formula (I) may be generated from the compound of formula (V) by an amide coupling reaction with an amine, most suitably with bis(2-methoxyethyl)amine.

For synthetic processes in which the compound of formula (II) is a protected derivative, the compound of formula (I) is revealed by an appropriate deprotection step, as is well known and practiced in the art. For example when the phenol present in the compound of formula (I) is protected with a silyl group, for example with a tertbutyldimethylsilyl group the deprotection step can be effected by treatment with a reagent such as tetrabutylammonium fluoride in the presence of a polar aprotic solvent such as DMF. The reaction may be performed at a reduced temperature, such as about 0° C.

Compounds of formula (II) can be prepared by reacting a compound of formula (VI):

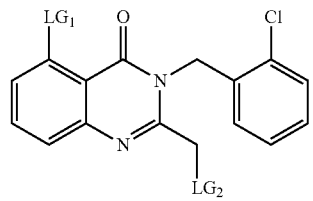

(VI)

or a protected derivative thereof, wherein $LG_1$ is a leaving group, as defined hereinabove for compounds of formula (II) and $LG_2$ is also a leaving group such as halo, for example a halogen atom and suitably a chlorine, with a compound of formula (VII):

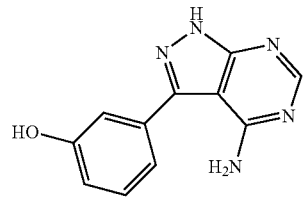

(VII)

or a protected derivative thereof, in the presence of a base and in a polar aprotic solvent.

Suitable bases for this transformation include potassium carbonate and a suitable polar aprotic solvent is DMF.

Synthetic processes include those for which is deemed advantageous to protect the phenolic hydroxyl of the compound of formula (VII) during the coupling step and suitable protected derivatives include a tertbutyldimethylsilyl ether and a tert-butyl ether.

Alternatively compounds of formula (II) can be prepared by reacting a compound of formula (VIII):

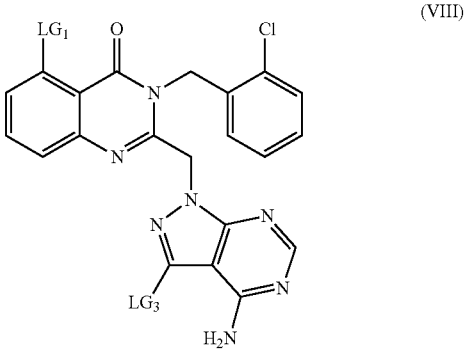

(VIII)

or a protected derivative thereof, wherein $LG_1$, is as defined above for compounds of formula (II) and $LG_3$ represents a leaving group such as halo, in particular iodo, with a compound of formula (IX):

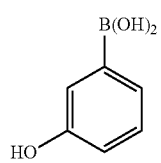

or a protected derivate thereof, in the presence of a suitable noble metal catalyst, an inorganic base and a polar protic solvent, under an inert atmosphere; followed, where appropriate, by deprotection.

A suitable catalyst is tetrakis(triphenylphosphine)palladium(0).

A suitable inorganic base is sodium carbonate and a suitable polar protic solvent is ethanol.

The reaction may be performed at an elevated temperature, for example at 85° C. for an extended period such as, for example, 3 days before cooling to RT.

Protecting groups may be advantageous to mask chemically sensitive groups during one or more of the reaction sequences described above, to ensure that one or more of the processes are efficient. Thus if desired or necessary, intermediate compounds may be protected by the use of conventional protecting groups. Protecting groups and means for their removal are described in "Protective Groups in Organic Synthesis", by Theodora W. Greene and Peter G. M. Wuts, published by John Wiley & Sons Inc; 4th Rev Ed., 2006, ISBN-10: 0471697540.

Novel intermediates are claimed as an aspect of the invention.

Advantageously, compounds of the present invention do not exhibit atropisomerism.

In one aspect the compound is useful in treatment, for example COPD and/or asthma.

The PI3K compounds developed to date have typically been intended for oral administration. Typically this strategy involves the optimisation of a compound's pharmacokinetic profile in order to achieve an adequate duration of action. In this way a sufficiently high drug concentration is established and maintained between doses to provide continuous clinical benefit. An inevitable and frequently undesired consequence of this approach is that non-targeted body tissues, especially the liver and the gut, are likely to be exposed to pharmacologically active concentrations of the drug.

An alternative strategy is to design treatment regimens in which the drug is dosed directly to the inflamed organ (for example topical therapy). Although this approach is not suitable for treating all chronic inflammatory conditions, it has been extensively exploited in treating lung diseases (asthma, COPD), skin lesions (atopic dermatitis and psoriasis), nasal diseases (allergic rhinitis) and gastrointestinal disorders (ulcerative colitis).

In topical therapy, the desired efficacy can sometimes be achieved by ensuring that the drug has a sustained duration of action and is retained predominantly in the target organ, thereby minimising the risks of systemic toxicity. Alternatively an appropriate formulation can be used which generates a "reservoir" of the active drug which is then available to sustain the desired effects. The first approach is exemplified in the use of the anticholinergic drug tiotropium bromide (Spiriva HandiHaler®), which is administered topically to the lung as a treatment for COPD. This compound has an exceptionally high affinity for its target receptor resulting in a very slow off rate (dissociation rate) and a consequent sustained duration of action.

There is provided according to one aspect of the present disclosure use of the compound of formula (I) or a suitable formulation derived therefrom, as a PI3 kinase inhibitor, for example administered topically to the lung.

In one aspect of the disclosure the compound herein is particularly suitable for topical delivery, such as topical delivery to the lungs, in particular for the treatment of COPD.

Thus is one aspect there is provided use of a compound of the invention for the treatment of COPD and/or asthma, in particular COPD or severe asthma, by inhalation i.e. by topical administration to the lung. Advantageously, administration to the lung allows the beneficial effects of the compounds to be realised whilst minimising the side-effects, for patients.

In one embodiment the compound is suitable for sensitizing patients to treatment with a corticosteroid.

The compound herein disclosed may also be useful for the treatment of rheumatoid arthritis.

Further, the present invention provides a pharmaceutical composition comprising a compound according to the disclosure optionally in combination with one or more pharmaceutically acceptable diluents or carriers.

Diluents and carriers may include those suitable for parenteral, oral, topical, mucosal and rectal administration, and may be different depending on the route of administration.

In one embodiment compositions may be prepared e.g. for parenteral, subcutaneous, intramuscular, intravenous, intra-articular or peri-articular administration, particularly in the form of liquid solutions or suspensions; for oral administration, particularly in the form of tablets or capsules; for topical e.g. pulmonary or intranasal administration, particularly in the form of powders, nasal drops or aerosols and transdermal administration; for mucosal administration e.g. to buccal, sublingual or vaginal mucosa, and for rectal administration e.g. in the form of a suppository.

The compositions may conveniently be administered in unit dosage form and may be prepared by any of the methods well-known in the pharmaceutical art, for example as described in Remington's Pharmaceutical Sciences, 17th ed., Mack Publishing Company, Easton, Pa., (1985).

Formulations for parenteral administration may contain as excipients sterile water or saline, alkylene glycols such as propylene glycol, polyalkylene glycols such as polyethylene glycol, oils of vegetable origin, hydrogenated naphthalenes and the like.

Formulations for nasal administration may be solid and may contain excipients, for example, lactose or dextran, or may be aqueous or oily solutions for use in the form of nasal drops or metered spray. For buccal administration typical excipients include sugars, calcium stearate, magnesium stearate, pregelatinated starch, and the like.

Compositions suitable for oral administration may comprise one or more physiologically compatible carriers and/or excipients and may be in solid or liquid form. Tablets and capsules may be prepared with binding agents, for example, syrup, acacia, gelatin, sorbitol, tragacanth, or poly-vinylpyrollidone; fillers, such as lactose, sucrose, corn starch, calcium phosphate, sorbitol, or glycine; lubricants, such as magnesium stearate, talc, polyethylene glycol, or silica; and surfactants, such as sodium lauryl sulfate. Liquid compositions may contain conventional additives such as suspending agents, for example sorbitol syrup, methyl cellulose, sugar syrup, gelatin, carboxymethyl-cellulose, or edible fats; emulsifying agents such as lecithin, or acacia; vegetable oils such as almond oil, coconut oil, cod liver oil, or peanut oil;

preservatives such as butylated hydroxyanisole (BHA) and butylated hydroxytoluene (BHT). Liquid compositions may be encapsulated in, for example, gelatin to provide a unit dosage form.

Solid oral dosage forms include tablets, two-piece hard shell capsules and soft elastic gelatin (SEG) capsules.

A dry shell formulation typically comprises of about 40% to 60% concentration of gelatin, about a 20% to 30% concentration of plasticizer (such as glycerin, sorbitol or propylene glycol) and about a 30% to 40% concentration of water. Other materials such as preservatives, dyes, opacifiers and flavours also may be present. The liquid fill material comprises a solid drug that has been dissolved, solubilized or dispersed (with suspending agents such as beeswax, hydrogenated castor oil or polyethylene glycol 4000) or a liquid drug in vehicles or combinations of vehicles such as mineral oil, vegetable oils, triglycerides, glycols, polyols and surface-active agents.

Suitably the compound of formula (I) is administered topically to the lung. Hence in one embodiment there is provided a pharmaceutical composition comprising a compound of the disclosure optionally in combination with one or more topically acceptable diluents or carriers. Topical administration to the lung may be achieved by use of an aerosol formulation. Aerosol formulations typically comprise the active ingredient suspended or dissolved in a suitable aerosol propellant, such as a chlorofluorocarbon (CFC) or a hydrofluorocarbon (HFC). Suitable CFC propellants include trichloromonofluoromethane (propellant 11), dichlorotetrafluoromethane (propellant 114), and dichlorodifluoromethane (propellant 12). Suitable HFC propellants include tetrafluoroethane (HFC-134a) and heptafluoropropane (HFC-227). The propellant typically comprises 40% to 99.5% e.g. 40% to 90% by weight of the total inhalation composition. The formulation may comprise excipients including co-solvents (e.g. ethanol) and surfactants (e.g. lecithin, sorbitan trioleate and the like). Aerosol formulations are packaged in canisters and a suitable dose is delivered by means of a metering valve (e.g. as supplied by Bespak, Valois or 3M).

Topical administration to the lung may also be achieved by use of a non-pressurised formulation such as an aqueous solution or suspension. This may be administered by means of a nebuliser. Topical administration to the lung may also be achieved by use of a dry-powder formulation. A dry powder formulation will contain the compound of the disclosure in finely divided form, typically with a mass mean diameter (MMAD) of 1-10 µm. The formulation will typically contain a topically acceptable diluent such as lactose, usually of large particle size e.g. a mass mean diameter (MMAD) of 100 µm or more. Example dry powder delivery systems include SPINHALER, DISKHALER, TURBOHALER, DISKUS, SKYEHALER, ACCUHALER and CLICKHALER.

In one embodiment a compound of the present invention is provided as a micronized dry powder formulation, for example comprising lactose of a suitable grade, filled into a device such as DISKUS.

The compound according to the disclosure is intended to have therapeutic activity. In a further aspect, the present invention provides a compound of the disclosure for use as a medicament.

The compound according to the disclosure may also be useful in the treatment of respiratory disorders including COPD (including chronic bronchitis and emphysema), asthma, paediatric asthma, cystic fibrosis, sarcoidosis, idiopathic pulmonary fibrosis, allergic rhinitis, rhinitis, sinusitis, especially asthma, chronic bronchitis and COPD.

The compound of the disclosure may also re-sensitise the patient's condition to treatment with a corticosteroid, when previously the patient's condition had become refractory to the same.

In one embodiment of the invention a dose of the present compound is employed that is equal to that suitable for use as a monotherapy but administered in combination with a corticosteriod.

In one embodiment a dose of the compound of formula (I) that would be subtherapeutic as a single agent is employed, in combination with a corticosteriod, thereby restoring patient responsiveness to the latter, in instances where the patient had previously become refractory to the same.

Additionally, the compound of the disclosure may exhibit anti-viral activity and prove useful in the treatment of viral exacerbations of inflammatory conditions such as asthma and/or COPD.

The compound of the present disclosure may also be useful in the prophylaxis, treatment or amelioration of flu virus, rhinovirus and/or respiratory syncytical virus.

The compound of formula (I), according to the disclosure is also expected to be useful in the treatment of certain conditions which may be treated by topical or local therapy including allergic conjunctivitis, conjunctivitis, allergic dermatitis, contact dermatitis, psoriasis, ulcerative colitis, inflamed joints secondary to rheumatoid arthritis or osteoarthritis.

In one embodiment the compound of formula (I) is considered useful in the, treatment of Hepatitis C and/or HIV, when administered by an appropriate route. Appropriate routes of administration may include oral, intravenous injection or infusion.

In one embodiment a compound of formula (I) for the treatment of Hepatitis C is delivered to the blood pre-entry to the liver.

The compound of the disclosure is also expected to be useful in the treatment of certain other conditions including rheumatoid arthritis, pancreatitis, cachexia, inhibition of the growth and metastasis of tumours including non-small cell lung carcinoma, breast carcinoma, gastric carcinoma, colorectal carcinomas and malignant melanoma.

In one embodiment the presently disclosed compound and pharmaceutical formulations comprising the same are useful in the treatment or prevention of cancer, in particular lung cancer, especially by topical administration to the lung.

Thus, in a further aspect, the present invention provides a compound as described herein for use in the treatment of one or more of the above mentioned conditions.

In a further aspect, the present invention provides use of a compound as described herein for the manufacture of a medicament for the treatment of one or more of the above mentioned conditions.

In a further aspect, the present invention provides a method of treatment of the above mentioned conditions which comprises administering to a subject an effective amount of a compound of the disclosure or a pharmaceutical composition thereof.

Compounds described herein may also be used in the manufacture of a medicament for the treatment of one or more of the above-identified diseases.

The word "treatment" is intended to embrace prophylaxis as well as therapeutic treatment.

A compound of the disclosure may also be administered in combination with one or more other active ingredients e.g. active ingredients suitable for treating the above mentioned conditions. For example possible combinations for treatment of respiratory disorders include combinations with steroids (e.g. budesonide, beclomethasone dipropionate, fluticasone propionate, mometasone furoate, fluticasone furoate), beta agonists (e.g. terbutaline, salbutamol, salmeterol, formoterol, indacaterol) and/or xanthines (e.g. theophylline), musacarinic antagonists, (e.g. ipratropium) and/or a p38 MAP kinase inhibitor.

In one embodiment a compound of the disclosure is administered in combination with an antiviral agent, for example acyclovir, tamiflu, relenza or interferon.

In one embodiment the combination of active ingredients are co-formulated.

In one embodiment a compound of the present disclosure is co-formulated with a corticosteriod as a formulation for inhalation, for example for use in maintenance therapy of COPD or lung cancer including prevention of the latter.

In one embodiment the combination of active ingredients is simply co-administered.

In one embodiment the compound of the disclosure is adminstered by inhalation and a corticosteriod is adminstered orally or by inhalation either in combination or separately.

EXPERIMENTAL SECTION

Abbreviations used herein are defined below (Table 1). Any abbreviations not defined are intended to convey their generally accepted meaning.

TABLE 1

| Abbreviations | |
|---|---|
| aq | aqueous |
| Ac | acetyl |
| ATP | adenosine-5'-triphosphate |
| BALF | bronchoalveolae lavage fluid |
| br | broad |
| BSA | bovine serum albumin |
| COPD | chronic obstructive pulmonary disease |
| d | doublet |
| DCM | dichloromethane |
| DMAP | 4-dimethylaminopyridine |
| DMSO | dimethyl sulfoxide |
| EDC•HCl | 1-ethyl-3-(3-dimethylaminopropyl)carbodiimide hydrochloride |
| (ES$^+$) | electrospray ionization, positive mode |
| Et | ethyl |
| EtOAc | ethyl acetate |
| EtOH | ethanol |
| FACS | fluorescence-activated cell sorting |
| FCS | foetal calf serum |
| FP | fluticasone propionate |
| g | gram(s) |
| HPLC-MS | high performance liquid chromatography mass spectrometry |
| hr | hour(s) |
| HRP | horseradish peroxidase |
| HRV | human rhinovirus |
| i-n | intra-nasal |
| i-t | intra-tracheal |
| IL-8 | interleukin 8 |
| μL | microliter(s) |
| LPS | lipopolysaccharide |
| μM | micromolar |
| M | molar |
| (M + H)$^+$ | protonated molecular ion |
| MCP-1 | monocyte chemoattractant protein |
| Me | methyl |
| MeOH | methanol |
| mg | milligram(s) |
| MHz | megahertz |
| min | minute(s) |
| mL | milliliter(s) |
| mM | millimolar |

TABLE 1-continued

| Abbreviations | |
|---|---|
| mmol | millimole(s) |
| MTT | 3-(4,5-dimethylthiazol-2-yl)-2,5-diphenyltetrazolium bromide |
| m/z | mass-to-charge ratio |
| ng | nanogram |
| nM | nanomolar |
| nm | nanometer |
| NMR | nuclear magnetic resonance (spectroscopy) |
| OVA | ovalbumin |
| PBS | phosphate buffered saline |
| Ph | phenyl |
| PIP2 | phosphatidylinositol 4,5-biphosphate |
| PIP3 | phosphatidylinositol 3,4,5-triphosphate |
| PMA | phorbol myristate acetate |
| po | by oral administration |
| PPh$_3$ | triphenylphosphine |
| q | quartet |
| quin | quintet |
| R$^t$ | retention time |
| RT | room temperature |
| RP HPLC | reverse phase high performance liquid chromatography |
| RSV | respiratory syncytial virus |
| s | singlet |
| SDS | sodium dodecyl sulfate |
| SEM | standard error of the mean |
| t | triplet |
| TMB | 3,3',5,5'-tetramethylbenzidine |
| TNFα | tumour necrosis factor alpha |
| TR-FRET | time-resolved fluorescence resonance energy transfer |
| vol | volume |

General Procedures

All starting materials and solvents were obtained either from commercial sources or prepared according to the literature citation. Unless otherwise stated all reactions were stirred. Organic solutions were routinely dried over anhydrous magnesium sulfate.

HPLC-MS was performed on Agilent HP1200 systems using Agilent Extend C18 columns, (1.8 μm, 4.6×30 mm) at 40° C. and a flow rate of 2.5-4.5 mL min$^{-1}$, eluting with a H$_2$O-MeCN gradient containing 0.1% v/v formic acid over 4 min. Gradient information: 0-3.00 min, ramped from 95% H$_2$O-5% MeCN to 5% H$_2$O-95% MeCN; 3.00-3.01 min, held at 5% H$_2$O-95% MeCN, flow rate increased to 4.5 mL min$^{-1}$, 3.01-3.50 min, held at 5% H$_2$O-95% MeCN, 3.50-3.60 min, returned to 95% H$_2$O-5% MeCN; flow rate reduced to 3.50 mL min$^{-1}$, 3.60-3.90 min, held at 95% H$_2$O-5% MeCN; 3.90-4.00 min, held at 95% H$_2$O-5% MeCN, flow rate reduced to 2.5 mL min$^{-1}$. UV detection was performed at 254 nm using an Agilent G1314B variable wavelength detector.

Mass spectra were obtained using electrospray ionization (ES) over the range m/z 60 to 2000 at a sampling rate of 1.6 sec/cycle using an Agilent G1956B, over m/z 150 to 850 at a sampling rate of 2 Hz using a Waters ZMD or over m/z 100 to 1000 at a sampling rate of 2 Hz using a Shimadzu 2010 LC-MS system. $^1$H NMR spectra were acquired on a Bruker Avance III spectrometer at 400 MHz using residual undeuterated solvent as reference.

5-Bromo-3-(2-chlorobenzyl)-2-(chloromethyl)quinazolin-4(3H)-one

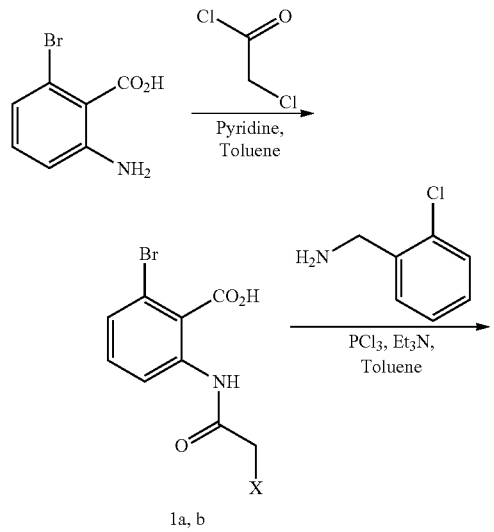

2-((4-Amino-3-iodo-1H-pyrazolo[3,4-d]pyrimidin-1-yl)methyl)-5-bromo-3-(2-chlorobenzyl)quinazolin-4(3H)-one

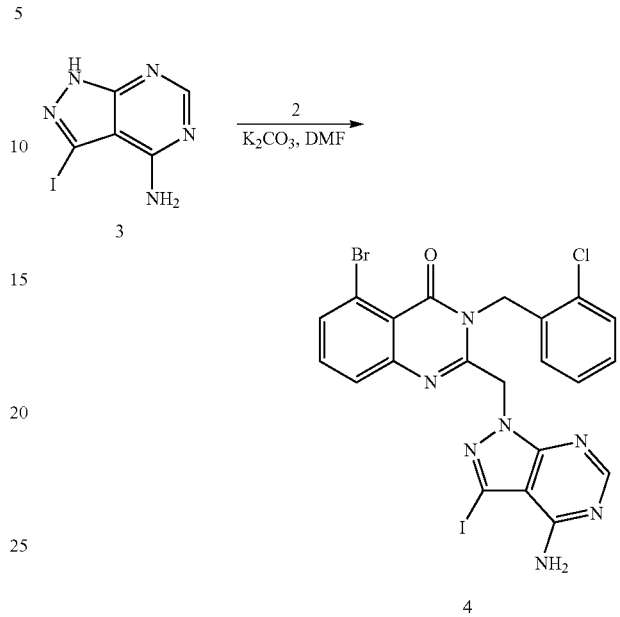

To a stirred solution of 2-amino-6-bromo-benzoic acid (3.06 g, 14.2 mmol) in toluene (75 mL) cooled to 0° C. in an ice-bath was added pyridine (0.60 mL, 7.10 mmol) followed by a solution of chloroacetyl chloride (2.26 mL, 28.4 mmol) in toluene (75 mL) drop-wise over 1 hr. The reaction mixture was allowed to warm to RT, and was heated at 115° C. for 3 hr and then allowed to cool to RT. The solvent volume was reduced by half by evaporation in vacuo. Upon standing overnight, the product precipitated and was collected by filtration to afford 2-bromo-6-(2-chloroacetamido)benzoic acid (1a, X=Cl) (1.44 g) as a white solid: m/z 290/292 (M+H)$^+$ (ES$^+$). The filtrate was concentrated in vacuo and the residue triturated with ethanol/heptane to afford 2-bromo-6-(2-hydroxyacetamido) benzoic acid (1b X=OH) (1.02 g, combined yield, 59%): m/z 274/276 (M+H)$^+$ (ES$^+$). Both 1a and 1b can be used without further purification in the next step.

To a stirred mixture of compound (1a) (7.50 g, 27.4 mmol), 2-chlorobenzylamine (5.00 mL, 41.05 mmol) and triethylamine (5.70 mL, 41.1 mmol) in toluene (250 mL) was added a solution of phosphorus trichloride (2.60 mL, 30.1 mmol) in toluene (250 mL) dropwise over 1 hr. The reaction mixture was heated to 110° C. for 24 hr, whereupon the hot solution was decanted and concentrated in vacuo. The residue was triturated with propan-2-ol (50 mL) to afford the title compound (2) (6.41 g, 59%) as a yellow solid: R$^t$ 2.67 min, m/z 397/399 (M+H)$^+$ (ES$^+$).

To a stirred mixture of 5-bromo-3-(2-chlorobenzyl)-2-(chloromethyl)quinazolin-4(3H)-one, (2), (13.6 g, 30.7 mmol) and 3-iodo-1H-pyrazolo[3,4-d]pyrimidin-4-amine (3) (8.09 g, 30.7 mmol) in DMF (300 mL was added potassium carbonate (6.36 g, 46.0 mmol) and the reaction maintained at RT in the dark for 24 hr. The mixture was poured onto water (4.0 L) and the resulting suspension was stirred at RT for 1 hr. The precipitate was isolated by filtration and dried in vacuo to afford the title compound, (4), as a colourless solid (18.0 g, 94%); R$^t$ 2.17 min, m/z 622/624 [M+H]$^+$ (ES$^+$).

3-(3-(tert-Butyldimethylsilyloxy)phenyl)-1H-pyrazolo[3,4-d]pyrimidin-4-amine

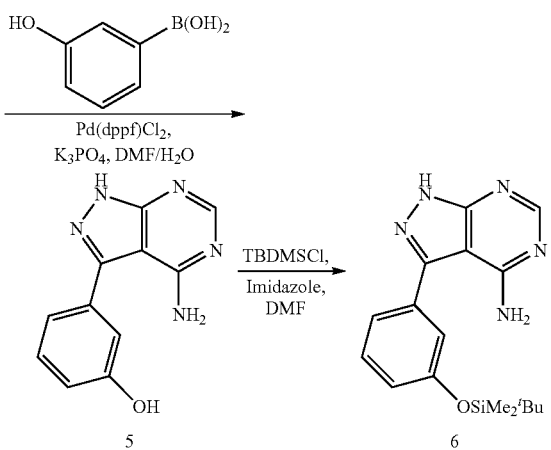

To a stirred suspension of 3-iodo-1H-pyrazolo[3,4-d]pyrimidin-4-amine (3) (8.22 g, 31.5 mmol), 3-phenol boronic acid (13.0 g, 94.5 mmol) and potassium phosphate (10.0 g, 47.3 mmol) in degassed DMF/water (3:2, 140 mL) was added [dppf] palladium (II) dichloride (13.0 g, 15.7 mmol). The reaction mixture was flushed with nitrogen, heated at 120° C. for 2 hr and then allowed to cool to RT. The reaction mixture was diluted with EtOAc (500 mL) and hydrochloric acid (2 M, 500 mL) and the resulting suspension was filtered. The filtrate was extracted with hydrochloric acid (2 M, 2×500 mL). The combined aq extracts were basified with a saturated aq solution of sodium carbonate to pH 10. The precipitate formed was filtered and the filtrate was extracted with EtOAc (3×1 L). The combined organic extracts were dried, filtered and the solvent removed in vacuo to afford a grey solid. All solid materials generated during the workup procedure were combined and triturated with DCM to afford 3-(4-amino-1H-pyrazolo[3,4-d]pyrimidin-3-yl)phenol (5) (6.04 g, 84%) as a grey solid: m/z 228 (M+H)$^+$ (ES$^+$).

To a stirred solution of the phenol (5) (4.69 g, 20.66 mmol) and imidazole (2.10 g, 30.99 mmol) in dry DMF (100 mL) was added TBDMSCl (4.70 g, 30.99 mmol). After 16 hr, further aliquots of imidazole (2.10 g, 30.99 mmol) and TBDMSCl (4.70 g, 30.99 mmol) were added and the mixture was stirred for 48 hr. The reaction mixture was diluted with water (120 mL) and extracted with DCM (2×200 mL). The combined organic extracts were washed with water (2×200 mL), dried, filtered and the volume reduced to approximately 100 mL by evaporation in vacuo. The resulting slurry was filtered and the solid washed with heptane (50 mL) to afford the title compound (6) (6.05 g, 85%) as an off-white solid: m/z 343 (M+H)$^+$ (ES$^+$).

Intermediate A: 2-((4-Amino-3-(3-hydroxyphenyl)-1H-pyrazolo[3,4-d]pyrimidin-1-yl)methyl)-5-bromo-3-(2-chlorobenzyl)quinazolin-4(3H)-one

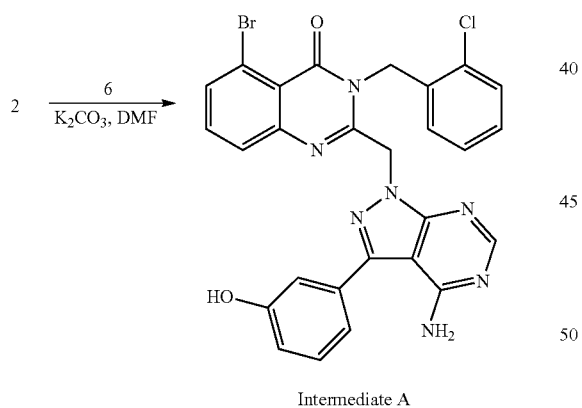

Intermediate A

To a stirred mixture of 5-bromo-3-(2-chlorobenzyl)-2-(chloromethyl)quinazolin-4(3H)-one (2) (100 mg, 0.25 mmol) and potassium carbonate (42 mg, 0.30 mmol) in DMF (2.5 mL) was added a solution of 3-iodo-1H-pyrazolo[3,4-d]pyrimidin-4-amine (3) (94 mg, 0.28 mmol) in DMF (2.5 mL) and the reaction mixture was stirred at RT for 18 hr. Potassium carbonate (3×35 mg, 0.75 mmol) was added in three portions over 30 hr. after which the solvent was removed in vacuo and the crude material was purified by flash column chromatography, eluting with 4.5% methanol in DCM, to afford the title compound, Intermediate A, (94 mg, 64%) as a off-white solid: R$^t$ 2.01 min; m/z 588/590 (M+H)$^+$, (ES$^+$).

Intermediate B:
N,N-bis(2-Methoxyethyl)hex-5-ynamide

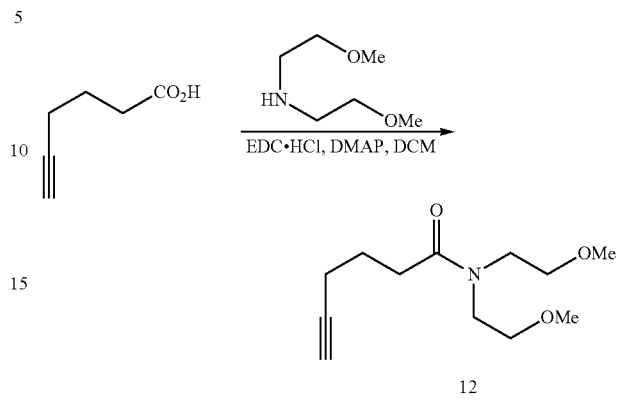

To a solution of hex-5-ynoic acid (7.11 g, 63.4 mmol), EDC.HCl (14.0 g, 72.9 mmol) and DMAP (387 mg, 3.17 mmol) in DCM (600 mL) at 0° C. was added bis(2-methoxyethyl)amine (9.3 mL, 63 mmol). The resulting mixture was warmed to RT for 20 hr and was then washed with hydrochloric acid (1 M, 2×500 mL) and water (500 mL). The organic layer was dried and evaporated in vacuo to afford the title compound, Intermediate B, as a yellow oil (16 g, 97%): $^1$H NMR (400 MHz, CDCl$_3$) δ: 1.88 (3H, m), 2.26 (2H, m), 2.49 (2H, m), 3.32 (6H, s), 3.51 (4H, m), 3.55 (4H, m)

6-(2-((4-Amino-3-(3-hydroxyphenyl)-1H-pyrazolo[3,4-d]pyrimidin-1-yl)methyl)-3-(2-chlorobenzyl)-4-oxo-3,4-dihydroquinazolin-5-yl)-N,N-bis(2-methoxyethyl)hex-5-ynamide: Compound of Formula (I)

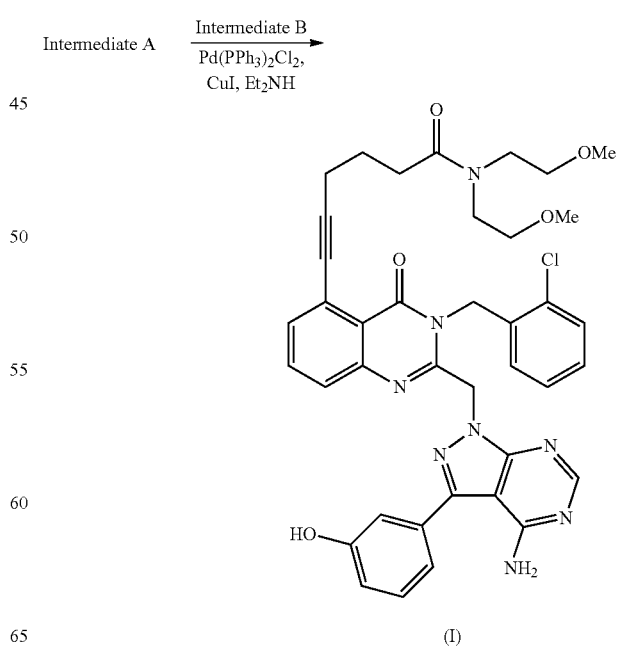

A mixture of Intermediate B (9.11 g, 34.9 mmol), bis-triphenylphosphine palladium(II) dichloride (0.98 g, 1.4 mmol), Intermediate A (8.3 g, 14 mmol), and copper(I) iodide (0.27 g, 1.4 mmol), in diethylamine (400 mL, 3.8 mol) was degassed with nitrogen and was then stirred at 60° C. for 4 hr then cooled to RT for a further 72 hr. The mixture was evaporated in vacuo and the residue was partitioned between aq ammonium acetate (500 mL) and EtOAc (500 mL). The organic layer was separated and was washed with brine (2×500 mL) and then dried and evaporated in vacuo. The residue was purified by flash column chromatography, ($SiO_2$, 120 g, MeOH in DCM, 0-5%, gradient elution) to afford the title compound of formula (I), as an off white solid (6.9 g, 66%): $R^t$ 1.92 min; m/z 735/737 $(M+H)^+$ $(ES^+)$ (Method D); $^1H$ NMR (400 MHz, DMSO-$d_6$) δ: 1.70 (2H, quin), 2.46 (2H, t), 2.55 (2H, t), 3.12 (3H, s), 3.19 (3H, s), 3.26 (2H, overlapping m), 3.31 (4H, m, partially obscured by HOD peak), 3.35 (2H, q), 5.30 (2H, s), 5.76 (2H, s), 6.18 (1H, dd), 6.80 (1H, dt), 6.85 (1H ddd), 6.92-6.94 (2H, overlapping m), 7.05 (1H, td), 7.13 (1H, dd), 7.31 (1H, t), 7.61 (1H, dd), 7.68 (1H, dd), 7.81 (1H, dd), 8.18 (1H, br s), 9.65 (1H, br s).

The additional complexity and consequences for drug development resulting from atropisomerism are analogous to those arising from other sources of molecular isomerism such as the presence of a stereogenic centre. This property renders such molecules both chiral, and unless resolved, a racemic mixture; the components of which could possess different pharmacological and toxicological profiles. This feature is likely to significantly increase downstream development costs for such molecules, and the absence of atropisomerism in the compound of formula (I) disclosed herein is therefore a highly desirable and advantageous property.

Biological Testing: Experimental Methods
Enzyme Inhibition Assay

PI3 kinases catalyse the phosphorylation of phosphatidylinositol 4,5-biphosphate (PIP2) to phosphatidylinositol 3,4,5-triphosphate (PIP3) in the presence of ATP and $Mg^{2+}$ ions. The PIP3 product can be detected by displacement of biotin-PIP3 from energy transfer complexes consisting of europium labelled anti-GST monoclonal antibody, a GST-tagged Pleckstrin homology (PH) domain, biotinylated PIP3 and streptavidin-allophycocyanin (APC) by the time-resolved fluorescence resonance energy transfer (TR-FRET) (HTRF®PI3K enzyme assay, Millipore). Excitation (330 nm) of europium in the complex results in an energy transfer to the APC and a fluorescent emission at 665 nm although europium itself emits at its characteristic 620 nm. The PIP3 product formed by PI3K activity displaces biotin-PIP3 from the complex and results in a loss of energy transfer (decreasing signal).

The compound to be tested was added, at the desired final concentrations, to a mixture of PIP2 substrate and recombinant PI3 kinase α, β or γ enzymes (Millipore), and the mixture incubated for 2 hr at RT. Following this incubation period, ATP (20 μM) was added to the enzyme/compound/PIP2 substrate mixture and the resulting mixture was incubated for 30 min at RT. A stopping solution containing biotinylated PIP3 and the detection mix containing the GST tagged GRP1 pleckstrin homology (PH) domain and fluorophores were then added and the mixture was incubated at RT for 15-18 hr, prior to detection in a fluorescence microplate reader (Varioskan® Flash, ThermoFisher Scientific).

The results were calculated according to the formula: APC signal (emission at 665 nm)/europium signal:(emission at 620 nm)×$10^4$. The percentage inhibition of each reaction was calculated relative to DMSO treated control, and the 50% inhibitory concentration ($IC_{50}$ value) then calculated from the concentration-response curve.

PI3Kδ Cell Based Assay

As a means of assessing PI3K δ activation in response to stimuli, the phosphorylation status of the protein, Akt, a downstream product of PI3Kδ, signaling was determined.

Human monocytic cells (U937 cells), were differentiated to macrophage-type cells by incubation with PMA (100 ng/mL) for 48 to 72 hr. Cells were then pre-incubated with either the test compound or vehicle for 2 hr and were then stimulated briefly by exposure to $H_2O_2$ (10 mM; 5-7 min) and the reaction stopped by replacing the media with 4% formaldehyde solution. Endogenous peroxide activity and formaldehyde were inactivated by incubating with quenching buffer (0.1% sodium azide, 1% $H_2O_2$ in PBS with 0.1% Triton X-100) for 20 min. The cells were washed with buffer (PBS containing 0.1% Triton X-100) and were incubated with blocking solution (1% BSA in PBS) for 1 hr and were then re-washed with buffer and incubated overnight with either anti-pAkt antibody or anti-pan-Akt antibody (both from Cell Signaling Technology). After washing with buffer (PBS containing 0.1% Triton X-100), cells were incubated with an HRP-conjugated secondary antibody (Dako) and the resultant signal was determined colorimetrically (OD: 450 nm with a reference wavelength of 655 nm) using TMB substrate (substrate reagent pack supplied by R&D Systems, Inc.).

This reaction was stopped by addition of 100 μL of 1N $H_2SO_4$ solution. Cells were then washed with buffer (PBS containing 0.1% Triton X-100) and 100 μL of 5% crystal violet solution was applied for 30 min. After washing with buffer (PBS containing 0.1% Triton X-100) 100 μL of 1% SDS was added to each well and the plates were shaken lightly for 1 hr prior to measuring the absorbance at 595 nm (Varioskan® Flash, Thermo-Fisher Scientific). The measured $OD_{450-655}$ readings were corrected for cell number by dividing the $OD_{450-655}$ by the $OD_{595}$ readings. The ratio of pAkt signal to total Akt signal was used to quantitate the extent of PI3K δ activation. The percentage inhibition for each well was calculated relative to a 10 μg/mL standard control (LY294002) set to 100% inhibition versus $H_2O_2$-only controls as 0% inhibition. The $IC_{50}$ values were calculated from the concentration-response curves generated by the serial dilutions of the test compounds.

PI3K γ Cell Based Assay

As a means of assessing the activation of PI3K γ in response to stimuli, the phosphorylation status of the protein, Akt, a downstream product of PI3K γ, signalling was determined following stimulation with MCP-1.

Human monocytic cells (THP1 cells) were pre-incubated in 1% FCS RPMI-1640 media for 1 hr. Cells were then treated with either the test compound or vehicle for 1 hr and stimulated briefly by exposure to MCP-1 (50 nM, 5-7 min; R&D systems, MN, USA). The reaction was stopped by replacing the media with 4% formaldehyde solution followed by permeabilisation using IntraPrep™ (Beckman Coulter, France) following the manufacturer's instructions. The cells were washed with washing buffer (PBS containing 0.1% BSA) and then incubated with anti-phospho-Akt (#9271 Cell Signaling, Danvers, Mass., USA) for 15 min at RT. After washing with washing buffer, cells were incubated with a Pacific blue-conjugated goat anti-rabbit antibody (Life Technologies Corp., Carlsbad, Calif., USA) and the fluorescence level was determined using an ATTUNE flow cytometer (Life Technologies Corp.). From the histogram, the minimum percentage of positive cells was calculated in each sample compared with baseline control and used to quantitate the extent of PI3K γ activation. The percentage inhibition for each well was calculated relative to a 10 μg/mL standard control (LY294002) set to 100% inhibition versus MCP1-only controls as 0% inhibition. The $IC_{50}$ value was calculated from the concentration-response curves generated by the serial dilutions of the test compounds.

Rhinovirus-Induced IL-8 Release

Human rhinovirus RV16 was obtained from the American Type Culture Collection (Manassas, Va.). Viral stocks were generated by infecting Hela cells with HRV until 80% of the cells were cytopathic. BEAS2B cells were infected with HRV at an MOI of 5 and incubated for 2 hr at 33° C. with gentle shaking to promote absorption. The cells were then washed with PBS, fresh media was added and the cells were incubated for a further 72 hr. The supernatant was collected for assay of IL-8 concentrations using a Duoset ELISA development kit (R&D systems, Minneapolis, Minn.).

In Vitro RSV Virus Load in Primary Bronchial Epithelial Cells

NHBEC (normal human bronchial epithelial cells) grown in 96 well plates were infected with RSV A2 (Strain A2, HPA, Salisbury, UK; at an MOI of 0.001) in the LHC8 Media:RPMI-1640 (50:50) containing 15 mM magnesium chloride and incubated for 1 hr at 37° C. for adsorption. The cells were then washed with PBS, fresh media was added and the cells were incubated for 4 days. Where appropriate, cells were pre-incubated with the test compound or DMSO for 2 hr, and then added again after washout of virus.

The cells were fixed with 4% formaldehyde in PBS solution for 20 min, washed with washing buffer (PBS including 0.5% BSA and 0.05% Tween-20) and incubated with blocking solution (5% condensed milk in PBS) for 1 hr. Cells were then washed with washing buffer and incubated for 1 hr at RT with anti-RSV (2F7) F-fusion protein antibody (mouse monoclonal; lot 798760, Cat. No. ab43812, Abcam). After washing, cells were incubated with an HRP-conjugated secondary antibody (lot 00053170, Cat. No. P0447, Dako) and then TMB substrate (substrate reagent pack lot 269472, Cat. No. DY999, R&D Systems, Inc.) was added. This reaction was stopped by addition of 2N $H_2SO_4$ (50 μL) and the resultant signal was determined colorimetrically (OD: 450 nm with a reference wavelength of 655 nm) in a microplate reader (Varioskan® Flash, ThermoFisher Scientific). Cells were then washed and a 2.5% crystal violet solution (lot 8656, Cat. No. PL7000, Pro-Lab Diagnostics) was applied for 30 min. After washing with washing buffer, 100 μL of 1% SDS was added to each well, and plates were shaken lightly on the shaker for 1 hr prior to reading the absorbance at 595 nm. The measured $OD_{450-655}$ readings were corrected to the cell number by dividing the $OD_{450-655}$ by the $OD_{595}$ readings. The percentage inhibition for each well was calculated and the $IC_{50}$ value was calculated from the concentration-response curve generated by the serial dilutions of compound.

MTT Assay

PMA-differentiated U937 cells were pre-incubated with test compound for 4 hr in 5% FCS or 10% FCS for 24 hr. The supernatant was replaced with 200 μL of new media and 10 μL of MTT stock solution (5 mg/mL) added to each well. After 1 hr incubation, the media were removed, 200 μL of DMSO added to each well and the plates were shaken lightly for 1 hr prior to reading the absorbance at 550 nm. The percentage loss of cell viability was calculated for each well relative to vehicle (0.5% DMSO)-treatment.

In Vivo Screening: Pharmacodynamics and Anti-Inflammatory Activity

Ovalbumin-Induced Nasal Eosinophil and Neutrophil Accumulation in Mice

BALB/c mice (6-8 weeks old) were immunized with OVA (40 μg/kg i.p.) on day 1 and 5. In order to elicit local inflammatory responses in the nose, mice were repeatedly challenged intra-nasally (10 μL per nostril) on days 12-19 with OVA (3% OVA in saline). On day 19 non-fasted mice were dosed intra-nasally (10 μL/nostril) with either vehicle or test compound at T=−2 hr relative to the start of the final OVA challenge. At T=0, each animal received a final intra-nasal OVA (3%) challenge. After a further 8 hr, each animal was anaesthetized and nasal lavage was carried out by instilling 1 mL of PBS into the posterior nares via a rostrally implanted tracheal cannula extending to a position that was approximately 1 mm before the posterior nares. This procedure was repeated to give a yield of approximately 2 mL of lavage fluid. Total cell numbers in the nasal lavage fluid samples were measured using a haemocytometer. Cytospin smears of the nasal lavage fluid samples were prepared by centrifugation at 1200 rpm for 2 min at RT and stained using a DiffQuik stain system (Dade Behring) for differential cell counts. Cells were counted using oil immersion microscopy. Data is expressed as differential number of cells per mL of nasal lavage fluid, mean±S.E.M.

Poly-I.C-Induced Cell Accumulation in Mice

Specific pathogen-free NJ mice (males, 5 weeks old) were administered with poly (I:C)-LMW (poly-IC; 1 mg/mL, 40 μL, in; InvivoGen, San Diego, Calif., USA) intranasally twice daily for 3 days under anaesthasia with 3% isoflurane. Test substances were given intra-nasally (35 μL of solution in 50% DMSO/PBS) 2 hr before each poly-I:C treatment. Twenty four hr after the last poly-I:C challenge, animals were anesthetized, the trachea cannulated and BALF was collected. The concentrations of alveolar macrophages and neutrophils in BALF were determined by FACS analysis (EPICS® ALTRA II, Beckman Coulter, Inc., Fullerton, Calif., USA) using anti-mouse MOMA2 antibody (macrophage) or anti-mouse 7/4 antibody (neutrophil).

Cigarette Smoke Model

A/J mice (males, 5 weeks old) were exposed to cigarette smoke (4% cigarette smoke, diluted with compressed air) for 30 min/day for 11 days using a Tobacco Smoke Inhalation Experiment System for small animals (Model SIS-CS; Sibata Scientific Technology, Tokyo, Japan). Test substances were given intra-nasally (35 μL of solution in 50% DMSO/

PBS) and therapeutically twice daily for 3 days after the final cigarette smoke exposure. Twelve hr after the last dosing, animals were anesthetized, the trachea cannulated and bronchoalveolar lavage fluid (BALF) was collected. The numbers of alveolar macrophages and neutrophils were determined by FACS analysis (EPICS® ALTRA II, Beckman Coulter, Inc., Fullerton, Calif., USA) using anti-mouse MOMA2 antibody (macrophage) or anti-mouse 7/4 antibody (neutrophil).

Summary of In Vitro and In Vivo Screening Results

The in vitro profile of the compound of formula (I) disclosed herein, as determined using the methods described above is presented below (Tables 2 and 3). The compound of the present invention demonstrates potent inhibition of both PI3 kinase δ and γ isoforms, and shows only modest inhibitory activity versus PI3 kinase α in enzyme assays. These effects translate into potent inhibition of Akt phosphorylation induced by the stimulation of cells with either hydrogen peroxide or MCP-1, as well as an inhibitory activity versus HRV-induced IL-8 release and RSV-induced F-protein expression in epithelial cells. No effects on cell viability, resulting from incubation with the compound of formula (I), were detected.

TABLE 2

Effects of the compound of formula (I) on PI3K isoforms; on cellular, hydrogen peroxide or MCP-1 induced phosphylation of Akt and on cell viability

| PI3 Kinase Inhibition $IC_{50}$ value at stated isozyme (nM) | | | Cellular Activity $IC_{50}$ values for inhibition of induced Akt phosphorylation | | Cell Viability MTT Assay in d-U937 cells[a] | |
|---|---|---|---|---|---|---|
| | | | $H_2O_2$ stimulus in | MCP-1 stimulus in | at | at |
| δ | γ | α | d-U937 cells | THP1 cells | 4 hr | 24 hr |
| 12 | 25 | 193 | 1.1 | 46 [b] | −ve | −ve |

[a]−ve indicates a value of <30% inhibition;
[b] calculated $IC_{50}$ value by linear regression.

TABLE 3

Effects of the compound of formula (I) on HRV-induced IL-8 release and on RSV-induced F-protein expression

| HRV16-induced IL-8 release in BEAS2B cells (% inhibition) | RSV F protein expression in bronchial epithelial cells: $IC_{50}$ value (nM) |
|---|---|
| 78% (at 0.1 μg/mL) | 389 |

Treatment of mice intra-nasally with the compound disclosed herein was found to produce a dose-dependent inhibition of both eosinophil and neutrophil accumulation in nasal lavage following allergen challenge (Table 4).

TABLE 4

The effects of treatment with the compound of formula (I) on OVA-induced airway eosinophilia and neutrophilia in mice.

| Compound (I) | Cell numbers in nasal lavage fluid ($\times 10^5$/mL) and (% inhibition) | |
|---|---|---|
| (mg/mL) | Eosinophils | Neutrophils |
| Vehicle | 1.51 ± 0.22 | 0.34 ± 0.06 |
| 0.05 | 1.13 ± 0.16 (25) | 0.27 ± 0.04 (21) |
| 0.2 | 0.57 ± 0.14 (62) | 0.15 ± 0.04 (56) |

N = 8 per group

The effect of treatment with the compound of the present invention on macrophage and neutrophil accumulation in BALF following exposure of mice to poly-I:C was also investigated. Treatment with compound of formula (I) was found to produce a dose-dependent inhibition of poly-I:C-induced macrophage and neutrophil accumulation into BALF (Table 5).

TABLE 5

The effects of treatment with the compound of formula (I) on poly-I:C-induced cell accumulation in mice airways.

| Treatment and dose of Compound of formula (I) | Cell numbers in BAL × $10^4$/mL (% inhibition) | |
|---|---|---|
| (mg/mL) | Macrophages | Neutrophils |
| Vehicle | 5.0 ± 0.90 | 3.0 ± 0.55 |
| Vehicle + Poly I:C | 16.7 ± 1.6 | 11.8 ± 0.3 |
| Poly I:C + (I) (0.002) | 13.8 ± 0.48 (25) | 10.8 ± 0.59 (11) |
| Poly I:C + (I) (0.02) | 12.2 ± 0.29 (38) | 9.4 ± 0.26 (27) |
| Poly I:C + (I) (0.2) | 9.4 ± 0.75 (61) | 7.9 ± 0.74 (44) |
| Poly I:C + (I) (2) | 6.4 ± 1.2 (88) | 5.6 ± 0.66 (70) |

The data for cell numbers are shown as the mean ± SEM, N = 5

The effects of treatment with the compound of formula (I) on macrophage and neutrophil accumulation in BALF following exposure to cigarette smoke were determined (Table 6). The cigarette smoke model used for this study is reported to

TABLE 6

The effect of treatment with the compound of fomula (I) ± fluticasone propionate on cigarette smoke-induced cell accumulation in murine BALF.

| Treatment[a] and dose of Compound of formula (I) | Cell numbers in BAL × $10^4$/mL[b] (% inhibition) | |
|---|---|---|
| (μg/mL) | Macrophages | Neutrophils |
| Air + Vehicle (0) | 3.9 ± 0.75 | 2.3 ± 0.33 |
| T + Vehicle (0) | 20.1 ± 1.3 | 18.3 ± 2.2 |
| T + (I) (20) | 14.9 ± 0.65 (32) | 13.0 ± 0.55 (33) |
| T + (I) (200) | 10.6 ± 0.02 (59) | 10.2 ± 0.83 (51) |
| T + (I) (2000) | 7.2 ± 0.40 (80) | 6.5 ± 0.55 (91) |
| T + (I) (2) + FP | 13.7 ± 0.63 (40) | 12.4 ± 1.0 (37) |
| T + (I) (20) + FP | 10.1 ± 0.70 (62) | 8.3 ± 0.72 (63) |
| T + (I) (200) + FP | 5.8 ± 0.48 (90) | 4.5 ± 0.49 (86) |

[a]T = tobacco smoke, FP = fluticasone propionate dosed at 50 μg/mL;
[b]The data for cell numbers are shown as the mean ± SEM, N = 5.

be a corticosteroid refractory system, [To, Y. et al., *Am. J. Respir. Crit. Care Med.*, 2010, 182:897-904; Medicherla, S. et al., *J. Pharmacol. Exp. Ther.* 2008, 324:921-9] and the data reveal that dexamethasone (0.3-10 mg/kg, p.o.) was, as anticipated, inactive. The effects of treatment with the compound of formula (I) on BALF neutrophils and on activated alveolar macrophage numbers demonstrate that it possesses anti-inflammatory activity when administered as a monotherapy. Moreover, when the compound of the present disclosure was co-administered with fluticasone propionate, at a dose which lacks any significant effect as monotherapy, a marked enhancement of anti-inflammatory activity was detected.

In summary, the compound of the invention is a potent inhibitor of both PI3 kinase δ and γ isoforms. The in vitro profile translates into a broad anti-inflammatory phenotype in vivo. In this setting, the inhibitory effects of the compound disclosed herein versus Poly I:C-induced cell accumulation in the airways is notable. It is also particularly striking that, unlike selective inhibitors of PI3 kinase δ, treatment with the compound disclosed herein alone results in marked inhibition of cigarette-smoke induced airways inflammation and that these effects occur at lower doses when it is co-adminstered with a corticosteroid, fluticasone propionate, under conditions where treatment with the corticosteroid alone is without effect.

Throughout the specification and the claims which follow, unless the context requires otherwise, the word 'comprise', and variations such as 'comprises' and 'comprising', will be understood to imply the inclusion of a stated integer, step, group of integers or group of steps but not to the exclusion of any other integer, step, group of integers or group of steps.

All patents and patent applications referred to herein are incorporated by reference in their entirety.

The invention claimed is:

1. A dry powder pharmaceutical formulation for inhalation comprising:

a compound of formula (I)

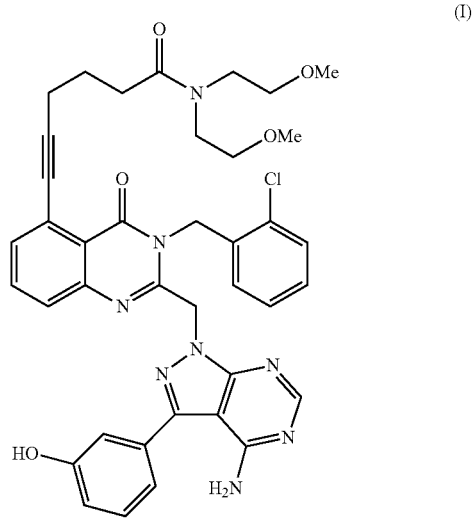 [SMILES: COCCN(CCOC)C(=O)CCCC#Cc1cccc2nc(Cn3nc(-c4cccc(O)c4)c4c(N)ncnc43)n(Cc3ccccc3Cl)c(=O)c12]

(I)

that is 6-(2-((4-amino-3-(3-hydroxyphenyl)-1H-pyrazolo[3,4-d]pyrimidin-1-yl) methyl)-3-(2-chlorobenzyl)-4-oxo-3,4-dihydroquinazolin-5-yl)-N,N-bis(2-methoxyethyl)hex-5-ynamide or a pharmaceutically acceptable salt thereof, including all stereoisomers, tautomers and isotopic derivatives thereof; and lactose as a topically acceptable diluent.

2. A dry powder pharmaceutical formulation according to claim 1, wherein the compound of formula (I) is in finely divided form.

3. A dry powder pharmaceutical formulation according to claim 2, wherein the compound of formula (I) has a mass median diameter (MMAD) of 1-10 μm.

4. A dry powder pharmaceutical formulation according to claim 1, wherein the compound of formula (I) is micronized.

5. A dry powder pharmaceutical formulation according to claim 1, wherein the compound of formula (I) is in free base form.

* * * * *